United States Patent
Jain et al.

(10) Patent No.: US 11,544,847 B1
(45) Date of Patent: Jan. 3, 2023

(54) SYSTEM AND METHOD FOR GENERATING POINT CLOUD DATA FOR ELECTRO-ANATOMICAL MAPPING

(71) Applicant: Neucures Inc., Los Angeles, CA (US)

(72) Inventors: Rohit Jain, Danville, CA (US); Robert L. Lux, Park City, UT (US)

(73) Assignee: NEUTRACE, INC., Longwood, FL (US)

( * ) Notice: Subject to any disclaimer, the term of this patent is extended or adjusted under 35 U.S.C. 154(b) by 260 days.

(21) Appl. No.: 17/073,268

(22) Filed: Oct. 16, 2020

(51) Int. Cl.
  G06K 9/00 (2022.01)
  G06T 7/00 (2017.01)
  G06T 17/20 (2006.01)
  A61M 25/01 (2006.01)
  A61B 5/06 (2006.01)

(52) U.S. Cl.
  CPC ............ G06T 7/0012 (2013.01); A61B 5/062 (2013.01); A61M 25/0127 (2013.01); G06T 17/20 (2013.01); G06T 2207/10028 (2013.01); G06T 2207/30048 (2013.01)

(58) Field of Classification Search
  CPC .................. G06T 7/0012; G06T 17/20; G06T 2207/10028; G06T 2207/30048; A61B 5/062; A61M 25/0127
  See application file for complete search history.

(56) References Cited

U.S. PATENT DOCUMENTS

| | | | |
|---|---|---|---|
| 2007/0299351 A1* | 12/2007 | Harlev | A61B 5/339 600/509 |
| 2008/0218509 A1* | 9/2008 | Voth | G06T 17/20 345/419 |
| 2017/0325891 A1* | 11/2017 | Harlev | A61B 34/25 |
| 2020/0046431 A1* | 2/2020 | Soper | A61B 1/2676 |
| 2020/0197106 A1* | 6/2020 | Dekel | A61B 5/065 |
| 2021/0174940 A1* | 6/2021 | Rodriguez | G06T 17/20 |

(Continued)

OTHER PUBLICATIONS

Manzke et al ("Automatic Segmentation of Rotational X-Ray Images . . . ", IEEE Transactions on Medical Imaging, vol. 29, No. 2, Feb. 2010) (Year: 2010).*

(Continued)

Primary Examiner — Shervin K Nakhjavan
(74) Attorney, Agent, or Firm — HM Law Group LLP; Vani Moodley, Esq.

(57) ABSTRACT

Disclosed is a method for generating high resolution point cloud data for electro-anatomical mapping comprising receiving sparsely measured point cloud data having a plurality of data points. Surface mesh data comprising mesh points defining triangles on a myocardial surface is generated. The point cloud data is mapped to the surface mesh data. For each point of the surface mesh data that cannot be mapped to the point cloud data because there is a missing data point in point cloud data, an interpolation operation is performed based on the point cloud data within the neighbourhood of the point to generate a value for the missing data point. The interpolation operation is repeated N times. For every repetition, a difference between the value for the missing data point generated from the current iteration and the value for the missing data point generated from the immediately preceding iteration is compared, until the difference is below a threshold.

12 Claims, 6 Drawing Sheets

(56) References Cited

U.S. PATENT DOCUMENTS

2022/0226046 A1* 7/2022 Mariappan ............. A61B 5/063

OTHER PUBLICATIONS

Porras et al ("Interventional Endocardial Motion Estimation . . . " IEEE Transactions on Biomedical Engineering, vol. 60 , No. 5, May 2013) (Year: 2013).*
Chan et al ("Intraprocedural fusion of electroanatomical maps . . . " Medical Imaging, 2007, San Diego, CA, United States) (Year: 2007).*

* cited by examiner

SYSTEM AND METHOD FOR GENERATING POINT CLOUD DATA FOR ELECTRO-ANATOMICAL MAPPING

CROSS-REFERENCE TO RELATED APPLICATIONS AND PRIORITY

The present application does not claim priority from any patent application.

TECHNICAL FIELD

Embodiments of the present invention relate to surface mapping. In particular, embodiments of the present invention relate to the generation of 3D point clouds for use in electro-anatomical mapping systems.

BACKGROUND

Electro-anatomical mapping (EAM) systems utilize various technologies to facilitate cardiac mapping and ablation. Data provided by EAM systems may include cardiac chamber reconstruction, tagging of important anatomic landmarks and ablation lesions, display of diagnostic and mapping catheters without using fluoroscopy, activation mapping, and voltage (or scar) mapping.

EAM depends upon data collection for procedural success (activation mapping, substrate mapping, cardiac geometry).

EAM systems generate cardiac geometry using point cloud data comprising a set of points wherein each point is defined by its spatial position within a coordinate system. In order to generate the point cloud data, a catheter is moved within the intra-cardiac space while its position is tracked within the said space through magnetic sensing. Typically, the catheter has a magnetic field-sensing tip whose spatial location can be tracked. The mapping process collects electrical recordings at a discrete at measurement sites where the catheter tip is in contact with the myocardial surface.

The electrical recordings from the measurement sites are analysed and enhanced with analytic metrics (calculations or measurements) to aid a clinician in determining underlying arrhythmia mechanisms. In order to accurately visualize the electrical wave front propagation and metric distributions on an electro-anatomical map, one must build estimated metric values at surface points on a high resolution surface with no measurement recordings.

SUMMARY

Before the present system and method for generating point cloud data for electro-anatomical mapping is described, it is to be understood that this application is not limited to the particular systems, and methodologies described, as there can be multiple possible embodiments which are not expressly illustrated in the present disclosure. It is also to be understood that the terminology used in the description is for the purpose of describing the particular versions or embodiments only and is not intended to limit the scope of the present application. This summary is provided to introduce concepts related to the system and method for generating point cloud data for electro-anatomical mapping. This summary is not intended to identify essential features of the claimed subject matter nor is it intended for use in determining or limiting the scope of the claimed subject matter.

In one implementation, a method for generating point cloud data for electro-anatomical mapping is disclosed. The method comprises receiving point cloud data comprising a plurality of data points (X, Y, and Z) generated pursuant to a data collection step. The method further comprises generating high resolution surface point and mesh data to represent a geometry of a myocardial surface. The surface mesh data may comprise one or more mesh points arranged to define triangles on the myocardial surface. The method may further comprise mapping the the sparsely measured point cloud data to the high resolution surface mesh data. Each data point in the point cloud data is mapped to a corresponding data point in the surface mesh data. Each data point (X,Y,Z) of the surface mesh data that cannot be mapped to a point cloud data because there is a missing data point (X,Y,Z) in the point cloud data, an interpolation operation is performed based on the point cloud data within the neighbourhood of the missing data point (X,Y,Z) to generate a value for the missing data point (X,Y,Z). Further the interpolation operation may be repeated N times. Each time the interpolation for the missing data point (X,Y,Z) is repeated, a check may be performed to compare a difference between the value for the missing data point (X,Y,Z) generated from the current iteration and the value for the missing data point (X,Y,Z) generated from the immediately preceding iteration; until the difference is below a threshold.

In another implementation, a system for generating point cloud data for electro-anatomical mapping is disclosed. The system comprises a memory and a processor coupled to the memory. The processor may be configured to execute instructions stored in the memory to receive point cloud data comprising a plurality of data points (X, Y, and Z) generated pursuant to a data collection step. The processor may be further configured to generate surface mesh data to represent a geometry of a myocardial surface. The surface mesh data may comprise one or more mesh points arranged to define triangles on the myocardial surface. The processor may be further configured to map the point cloud data to the surface mesh data. Each data point in the point cloud data may be mapped to a corresponding data point in the surface mesh data. Each data point (X,Y,Z) of the surface mesh data that cannot be mapped to a point cloud data because there is a missing data point (X,Y,Z) in the point cloud data, an interpolation operation may be performed based on the point cloud data within the neighbourhood of the missing data point (X,Y,Z) to generate a value for the missing data point (X,Y,Z). Further, the processor may be configured to repeat the interpolation operation N times. Each time the interpolation for the missing data point (X,Y,Z) is repeated, a check may be performed to compare a difference between the value for the missing data point (X,Y,Z) generated from the current iteration and the value for the missing data point (X,Y,Z) generated from the immediately preceding iteration; until the difference is below a threshold.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to refer like features and components.

DETAILED DESCRIPTION

Some embodiments of the present disclosure, illustrating all its features, will now be discussed in detail. The words "comprising", "receiving", "determining", "generating" and other forms thereof, are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a", "an" and "the" include plural references unless the context clearly dictates otherwise. Although any systems and methods similar or equivalent to those described herein can be used in the practice or testing of embodiments of the present disclosure, the exemplary system and method for generating point cloud data for electro-anatomical mapping are now described. The disclosed embodiments of the system and method for generating point cloud data for electro-anatomical mapping are merely exemplary of the disclosure, which may be embodied in various forms.

Various modifications to the embodiment will be readily apparent to those skilled in the art and the generic principles herein may be applied to other embodiments. However, one of ordinary skill in the art will readily recognize that the present disclosure for system and method for generating point cloud data for electro-anatomical mapping is not intended to be limited to the embodiments illustrated, but is to be accorded the widest scope consistent with the principles and features described herein.

As referred in the background, the conventional electro-anatomical mapping (EAM) systems utilize various technologies to facilitate mapping and ablation. EAM depends upon data collection for procedural success (activation mapping, substrate mapping, cardiac geometry). The conventional EAM systems generate cardiac geometry using point cloud data comprising a set of points wherein each point is defined by its spatial position within a coordinate system. In order to generate the point cloud data, a catheter is moved within the intra-cardiac space while its position is tracked within the said space through magnetic sensing. Typically, the catheter has a magnetic field-sensing tip whose spatial location can be tracked. The mapping process collects electrical recordings at discrete measurement sites where the catheter tip is in contact with the myocardial surface.

The electrical recordings from the measurement sites are analysed and enhanced with metrics to aid a clinician in determining underlying arrhythmia mechanisms. The electrical data may be sampled for only a limited number of data points leading to inaccuracy.

The present subject matter overcomes the problems associated with the conventional EAM systems. The present subject matter addresses the problems by using an interpolation technique for generating point cloud data for electro-anatomical mapping. The interpolation technique involves generating data values for intermediate regions on a geometric surface from a sparse collection of measurement sites.

The present subject matter relates to a method for generating point cloud data for electro-anatomical mapping. The method comprises receiving point cloud data comprising a plurality of data points (X, Y, and Z) generated pursuant to a data collection step. Further, surface mesh data is generated to represent a geometry of a myocardial surface. The surface mesh data comprises one or more mesh points arranged to define triangles on the myocardial surface.

Further, the point cloud data is mapped to the surface mesh data. Each data point in the point cloud data may be mapped to a corresponding data point in the surface mesh data. The mapping comprises, firstly for each data point (X,Y,Z) of the surface mesh data that cannot be mapped to a point cloud data because there is a missing data point (X,Y,Z) in the point cloud data, an interpolation operation is performed based on the point cloud data within the neighbourhood of the missing data point (X,Y,Z) to generate a value for the missing data point (X,Y,Z). Further the interpolation step may be repeated N times. Each time the interpolation for the missing data point (X,Y,Z) is repeated, a check may be performed to compare a difference between the value for the missing data point (X,Y,Z) generated from the current iteration and the value for the missing data point (X,Y,Z) generated from the immediately preceding iteration, until the difference is below a threshold.

Thus, the present subject matter aids in accurately visualizing the electrical wave front propagation on an electro-anatomical map, by building metric values at surface points with no measurement recordings. In other words, the method disclosed in the present subject matter generates point cloud data for electro-anatomical mapping considering every data point including missing data points with no measurement information. It is to be noted that the system may lead to an overall improvement in the process of generating point cloud data for electro-anatomical mapping.

Figure 1:
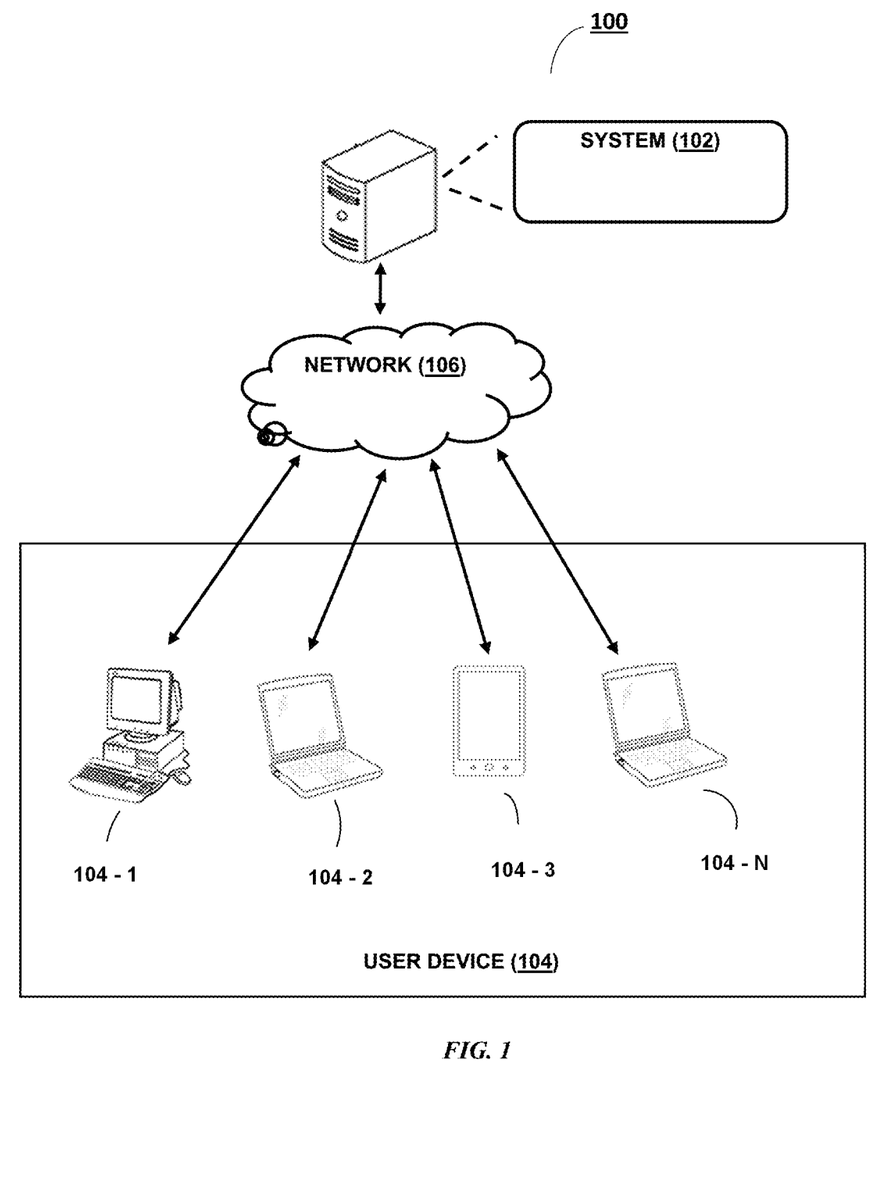
FIG. 1 illustrates a network implementation of a system 102 for generating point cloud data for electro-anatomical mapping, in accordance with an embodiment of the present subject matter.

Referring now to FIG. 1, a network implementation 100 of a system 102 for generating point cloud data for electro-anatomical mapping is disclosed. Although the present subject matter is explained considering that the system 102 is implemented on a server, it may be understood that the system 102 may also be implemented in a variety of computing systems, such as a laptop computer, a desktop computer, a notebook, a workstation, a mainframe computer, a server, a network server, and the like. In one implementation, the system 102 may be implemented over a cloud network. Further, it will be understood that the system 102 may be accessed by multiple users through one or more user devices 104-1, 104-2 . . . 104-N, collectively referred to as user device 104 hereinafter, or applications residing on the user device 104. Examples of the user device 104 may include, but are not limited to, a portable computer, a personal digital assistant, a handheld device, and a workstation. The user device 104 may be communicatively coupled to the system 102 through a network 106.

In one implementation, the network 106 may be a wireless network, a wired network or a combination thereof. The network 106 may be implemented as one of the different types of networks, such as intranet, local area network (LAN), wide area network (WAN), the internet, and the like.

The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further, the network 106 may include a variety of network devices, including routers, bridges, servers, computing devices, storage devices, and the like.

In one embodiment, the method for generating point cloud data for electro-anatomical mapping may comprise receiving point cloud data comprising a plurality of data points (X, Y, and Z) generated pursuant to a data collection step. The method may further comprise generating surface mesh data to represent a geometry of a myocardial surface. The surface mesh data may comprise one or more mesh points arranged to define triangles on the myocardial surface. The method may further comprise mapping the point cloud data to the surface mesh data. Each data point in the point cloud data may be mapped to a corresponding data point in the surface mesh data. Further, for each data point (X,Y,Z) of the surface mesh data that cannot be mapped to a point cloud data because there is a missing data point (X,Y,Z) in the point cloud data, an interpolation operation may be performed based on the point cloud data within the neighbourhood of the missing data point (X,Y,Z) to generate a value for the missing data point (X,Y,Z). Further the interpolation step may be repeated N times. Each time the interpolation for the missing data point (X,Y,Z) is repeated, a check may be performed to compare a difference between the value for the missing data point (X,Y,Z) generated from the current iteration and the value for the missing data point (X,Y,Z) generated from the immediately preceding iteration, until the difference is below a threshold.

Figure 2:
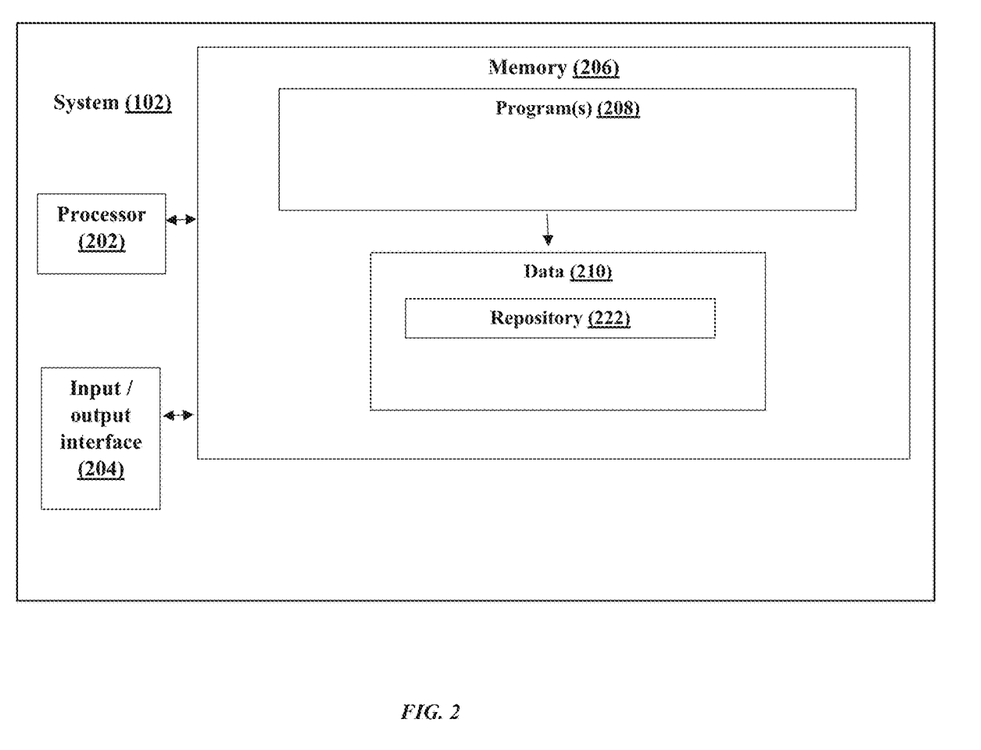
FIG. 2 illustrates a system 102 for generating point cloud data for electro-anatomical mapping, in accordance with an embodiment of the present subject matter.

Referring now to FIG. 2, a system 102 for generating point cloud data for electro-anatomical mapping illustrated in accordance with an embodiment of the present subject matter.

In one embodiment, the system 102 may include at least one processor 202, an input/output (I/O) interface 204, and a memory 206. The at least one processor 202 may be implemented as one or more microprocessors, microcomputers, microcontrollers, digital signal processors, central processing units, state machines, logic circuitries, and/or any devices that manipulate signals based on operational instructions. Among other capabilities, at least one processor 202 may be configured to fetch and execute computer-readable instructions stored in the memory 206.

The I/O interface 204 may include a variety of software and hardware interfaces, for example, a web interface, a graphical user interface, and the like. The I/O interface 204 may allow the system 102 to interact with the user directly or through the user device 104. Further, the I/O interface 204 may enable the system 102 to communicate with other computing devices, such as web servers and external data servers (not shown). The I/O interface 204 may facilitate multiple communications within a wide variety of networks and protocol types, including wired networks, for example, LAN, cable, etc., and wireless networks, such as WLAN, cellular, or satellite. The I/O interface 204 may include one or more ports for connecting a number of devices to one another or to another server.

The memory 206 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 206 may include one or more modules and data 210.

The modules may include routines, programs, objects, components, data structures, and the like, which perform particular tasks, functions or implement particular abstract data types. In one implementation, the module 206 may one or more programs a modules 2084 performing an interpolation technique as will be described with reference to FIG. 3.

The data 210, amongst other things, serve as a repository for storing data processed, received, and generated by the system 102.

In one implementation, a user may access the system 102 via the I/O interface 204. The user may be registered using the I/O interface 204 in order to use the system 102. In one aspect, the user may access the I/O interface 204 of the system 102 for obtaining information, providing input information or configuring the system 102.

In one embodiment, the system 102 may be configured to receive point cloud data through the I/O interface 204. The point cloud data may comprise a plurality of data points (X, Y, and Z). The plurality of data points (X, Y, and Z) may be generated pursuant to a data collection step. The point cloud data may be generated by a catheter comprising a magnetic field-sensing tip in contact with the myocardial surface. Also, the point cloud data may comprise data corresponding to at least one of a unipolar signal, a bipolar signal generated by the catheter. Further, the point cloud data may represent metrics selected from the group comprising activation times, and voltages.

Upon receiving the point cloud data, the system 102 may be configured to generate surface mesh data. The surface mesh data may represent a geometry of a myocardial surface. Further, the surface mesh data may comprise one or more mesh points arranged to define triangles on the myocardial surface.

Further, the system 102 may be configured to map the point cloud data to the surface mesh data. Each data point in the point cloud data may be mapped to a corresponding mesh point in the surface mesh data.

In one embodiment, each mesh point (X,Y,Z) of the surface mesh data may not be mapped to the point cloud data as the point cloud data may comprise one or more missing data points (X,Y,Z). Thus, an interpolation operation may be performed for each missing data point (X,Y,Z) by using a spatial interpolation technique, for example an iterative nearest neighbour construction algorithm. The nearest neighbour construction algorithm may comprise performing interpolation operation for each missing data point (X,Y,Z) based on the point cloud data within a neighbourhood of the data point (X,Y,Z) to generate a value for the missing data point (X,Y,Z).

In one embodiment, one or more immediate neighbour data points surrounding the missing data point (X,Y,Z) may be identified. Further, metric values associated with the one or more immediate neighbour data points are determined. Upon determining the metric values, an average of the metric values may be computed. The computed average metric value may be assigned to the missing data point (X,Y,Z). The averaging process may be repeated for any remaining missing data points (X,Y,Z) on the point cloud data.

In one embodiment, the step of interpolation may be repeated N times. The value of N may be as high as 10,000 or more. Each time the interpolation for the missing data point (X,Y,Z) is repeated, a check may be performed to compare a difference between the value for the missing data point (X,Y,Z) generated from the current iteration and the value for the missing data point (X,Y,Z) generated from the immediately preceding iteration; until the difference is below a threshold. In one embodiment, threshold may be said to be 0.001.

Figure 3:
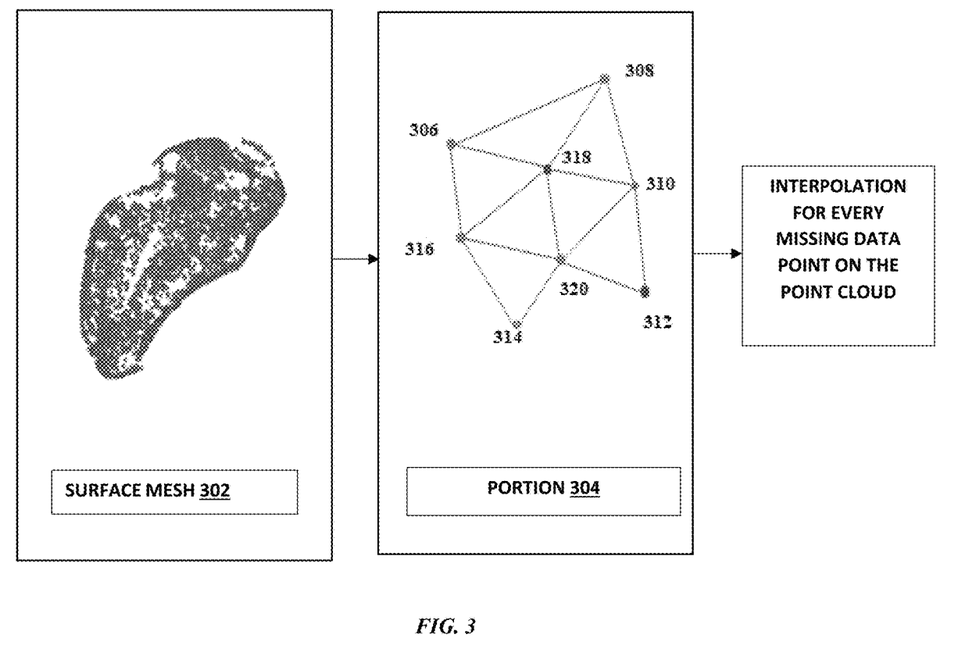
FIG. 3 illustrates an exemplary embodiment for an interpolation operation performed on point cloud data, in accordance with an embodiment of the present subject matter.

Referring now to FIG. 3, an exemplary embodiment for an interpolation operation performed on point cloud data, in accordance with an embodiment of the present subject matter, is shown.

In the exemplary embodiment, point cloud data comprising a plurality of data points is received through the I/O interface 204 and mapped to a surface mesh 302 representative of a myocardial surface. The surface mesh 302 comprises a plurality of mesh points arranged to define triangles on the myocardial surface. The mapping of each point cloud data point to a surface mesh data point is based on spatial correspondence between the points. Reference numeral 304 indicates a portion of the surface mesh 302 in greater detail to illustrate the interpolation technique of the present invention. As will be seen, the portion 304 comprises mesh points 306, 308, 310, 312, 314, 316, 318, and 320. In practice, the point cloud data may have missing data points so that not every mesh point on the mesh surface 302 may be mapped to a data point from the point cloud. The goal of the interpolation technique disclosed herein is to generate the missing data points, as will be described.

For illustrative purposes, consider that the mesh points 312, and 318. In accordance with the techniques disclosed herein, the missing data points are identified post the above-identified mapping step for the purpose of generating values for said missing data points. The value may be generated based on interpolation of the data by applying an iterative nearest neighbour construction algorithm. The iterative nearest neighbour construction algorithm involves identifying one or more immediate neighbour data points surrounding the missing data points. For example, this case of the mesh point 318, the one or more immediate neighbour data points surrounding the mesh point 318 are identified as the mesh points 306, 308, 310, 320, and 316. Further, metric values associated with each of these neighbouring points are determined, and an average of the metric values associated with each of these neighbouring points may be computed. The computed average metric value may be assigned to the mesh point 318. The averaging process is then repeated for any remaining missing data points.

The interpolation operation may be repeated N times. The value of N may be at least 10,000. Each time the interpolation for the missing data point is repeated, a check is performed to compare a difference between the value for the missing data point 318 generated from the current iteration and the value for the missing data point 318 generated from the immediately preceding iteration, until the difference is below a threshold.

Figure 4:
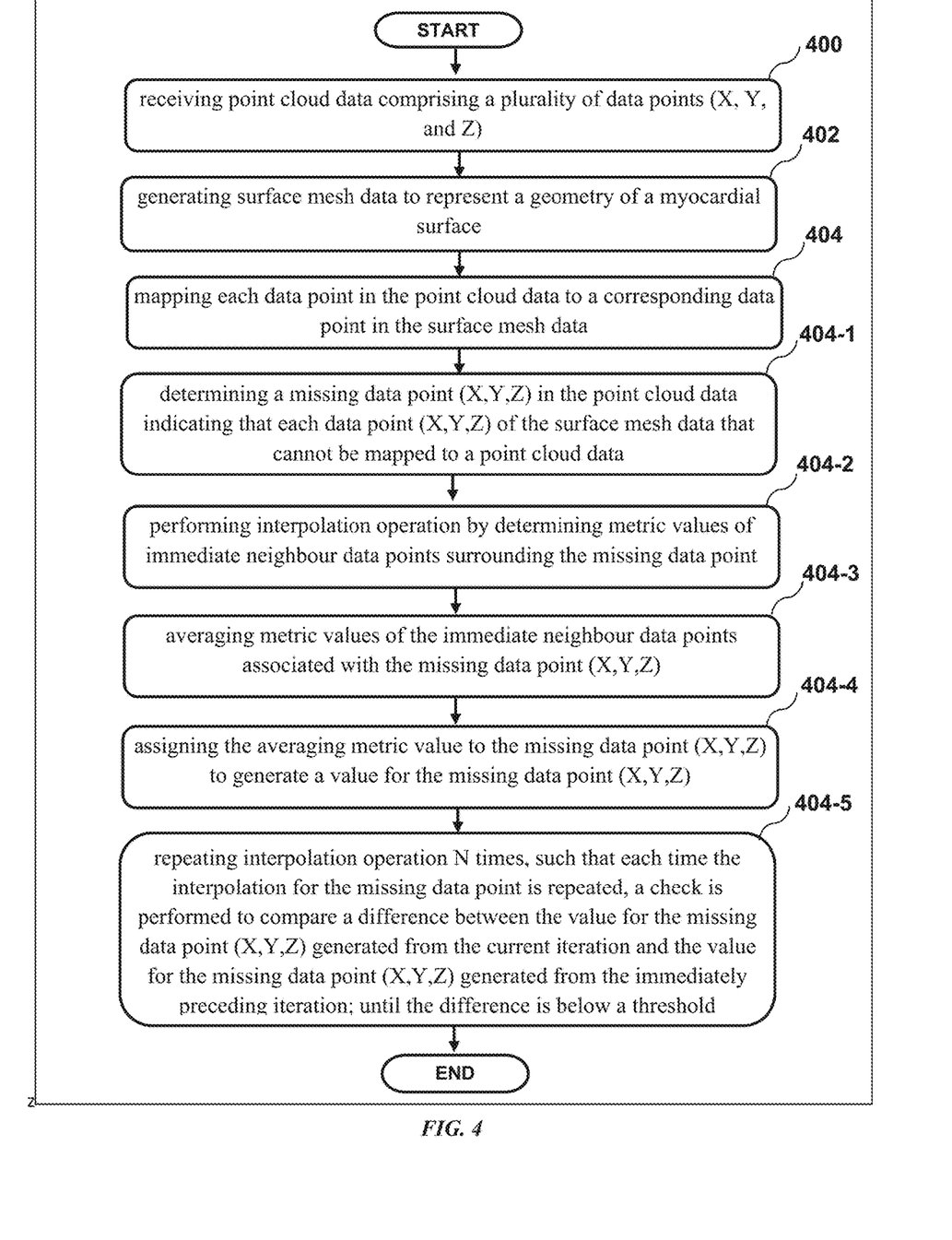
FIG. 4 illustrates a flow chart illustrating a method 400 for generating missing point cloud data during electro-anatomical mapping, in accordance with an embodiment of the present subject matter.

Referring now to FIG. 4, a flow chart illustrating a method 400 for generating missing point cloud data during electroanatomical mapping, is disclosed in accordance with an embodiment of the present subject matter.

The method may be described in the general context of computer executable instructions. Generally, computer executable instructions can include routines, programs, objects, components, data structures, procedures, modules, functions, and the like, that perform particular functions or implement particular abstract data types. The method 400 may also be practiced in a distributed computing environment where functions are performed by remote processing devices that are linked through a communications network. In a distributed computing environment, computer executable instructions may be located in both local and remote computer storage media, including memory storage devices.

The order in which the method is described is not intended to be construed as a limitation, and any number of the described method blocks can be combined in any order to implement the method or alternate methods. Additionally, individual blocks may be deleted from the method without departing from the spirit and scope of the subject matter described herein. Furthermore, the method can be implemented in any suitable hardware, software, firmware, or combination thereof. However, for ease of explanation, in the embodiments described below, the method may be considered to be implemented in the above described system 102.

Following to FIG. 4, at block 400, point cloud data may be received. The point cloud data may comprise a plurality of data points (X, Y, and Z). The plurality of data points (X, Y, and Z) may be generated pursuant to a data collection step. In one embodiment, the point cloud data may be generated by a catheter comprising a magnetic fieldsensing tip in contact with the myocardial surface. Also, the point cloud data may comprise at least one of a unipolar, a bipolar signal generated by the catheter. The point cloud data may represent metrics selected from the group comprising activation times, and voltages.

At block 402, surface mesh data may be generated. The surface mesh data may represent a geometry of a myocardial surface. Further, the surface mesh data may comprise one or more mesh points arranged to define triangles on the myocardial surface.

At block 404, the point cloud data may be mapped to the surface mesh data. Each data point (X,Y,Z) in the point cloud data may be mapped to a corresponding mesh point in the surface mesh data. However, each mesh point of the surface mesh data may not be mapped to the point cloud data, due to one or more missing data points (X,Y,Z) in the point cloud data. In order to generate the point cloud data, each missing data point and their associated values value is required to be identified.

At block 404-1, the missing data point (X,Y,Z) is identified for generating a value for the missing data point (X,Y,Z). The value may be generated based on interpolation of the data by applying an iterative nearest neighbour construction algorithm. The iterative nearest neighbour construction algorithm involves identifying one or more immediate neighbour data points surrounding the missing data point (X,Y,Z).

At block 404-2, one or more metric values associated with the one or more immediate neighbour data points are determined.

At block 404-3, upon determining the metric values, an average of the metric values may be computed.

At block 404-4, the computed average metric value may be assigned to the missing data point (X,Y,Z).

At block 404-5, the averaging process may be repeated for any remaining missing data points (X,Y,Z) on the point cloud data.

In one embodiment, the interpolation operation may be repeated N times. The value of N may be at least 10,000. Each time the interpolation for the missing data point (X,Y,Z) is repeated, a check may be performed to compare a difference between the value for the missing data point (X,Y,Z) generated from the current iteration and the value for the missing data point (X,Y,Z) generated from the immediately preceding iteration, until the difference is below a threshold. The difference value reaching below a threshold may indicate generation of values for the missing data points (X,Y,Z), thereby enabling generation of the point cloud data for electro-anatomical mapping.

Thus, the point cloud is generated for electro-anatomical mapping by generating values for each missing data point (X,Y,Z) in the point cloud data based on the iterative nearest neighbour construction algorithm.

Exemplary embodiments discussed above may provide certain advantages. Though not required to practice aspects of the disclosure, these advantages may include those provided by the following features.

Some embodiments of the system and the method enable generating a point cloud data from a sparse collection of data points.

Some embodiments of the system and the method enable building of metric values at data points on the point cloud data with no measurement recordings.

Some embodiments of the system and the method may be configured to perform interpolation method by simulating voltage propagation on a surface and building a more physiologically accurate distribution of data.

Some embodiments of the system and the method may be configured to accurately visualize the electrical wave front propagation on the 3D geometry.

Some embodiments of the system and the method may be configured to utilize the interpolation technique to propagate measurement information to non-measured sites on the point cloud data.

Some embodiments of the system and the method may be configured to produce wave front propagations simulating spirals, collisions and bifurcations as expected in clinical cases.

Although implementations for system and method for generating point cloud data for electro-anatomical mapping, it is to be understood that the appended claims are not necessarily limited to the specific features or methods described. Rather, the specific features and methods are disclosed as examples of implementations for generating point cloud data for electro-anatomical mapping.

Figure 5:
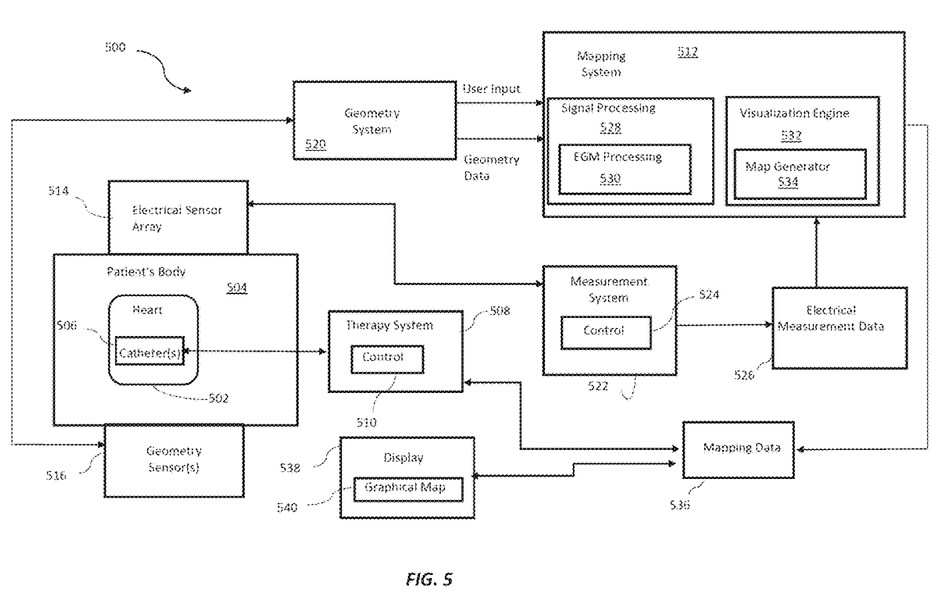
FIG. 5 of the drawings shows an exemplary diagnostic/treatment system, in accordance with one embodiment of the invention.

FIG. 5 of the drawings shows an exemplary diagnostic/treatment system 500, in accordance with one embodiment of the invention. The system 500 comprises geometry sensors and a geometry system capable of implementing the above-described techniques for generating point cloud data, as will be described. The system 500 is capable of assessing the condition of the heart 502 in real-time as part of a treatment or diagnostic procedure. For this purpose, the system 500 includes one or more catheters that can be inserted into a patient's body 504 thereby to contact the patient's heart 502—more specifically the endocardium or the epicardium. One of ordinary skill in the art would understand and appreciate that various types and configurations of catheters 506 may be utilized, depending on the type of treatment and procedure. In some cases, the therapy system 506 may include one or more electrodes located at the tip of an ablation catheter which in use is configured to ablate tissue in response to electrical signals (for example radiofrequency energy) supplied by a therapy system 508. In other cases, the therapy delivery device 506 may include one or more electrodes located at the tip of a pacing catheter to deliver electrical stimulation for pacing the heart.

The therapy system 508 may be located external to the patient's body 504 and may be configured to control the type of therapy that is delivered by the device 506. For example, the therapy system 508 may include control circuitry 510 configured to deliver electrical signals by a conductive link electrically connected between the device (electrodes) 506 and the therapy system 508. The control circuitry 510 may provide control parameters for the signals supplied to the device 506 (these may include current, voltage, etc.) For delivering therapy (example ablation) via the electrode (s) 504 to one or more sites within the heart 502, the control circuitry 510 may set therapy parameters and apply stimulation based on automatic, manual (user input) or a combination of automatic and manual mechanisms. In some embodiments, one or more sensors (not shown) may be configured to communicate since the information back to the therapy system 508. The position of the catheter 506 within the heart 502 may be determined and tracked by a mapping system 502. Location of the device 506 and in the therapy parameters may be combined to provide corresponding therapy parameters data.

In some embodiments, prior to providing therapy by the therapy system 508 and other system or subsystem may be utilized to acquire electrophysiological data for the patient. For this purpose, a sensor array 514 including one or more electrodes may be utilized for recording patient activity. In some cases, the sensor array 514 may include an arrangement of body surface sensors distributed over a portion of the patient's torso for measuring electrical activity associated with the patient's heart. The catheter 506 may include one or more electrodes that can be utilized in conjunction with the sensor array 514 for mapping electrical activity of the endocardial surface such as the wall of the heart chamber. Additionally, such electrodes may be used to obtain location or positional information of the catheter 506 within the heart which can advantageously be used to register electrical information of the heart in an image or map is generated by the system 500. In some embodiments, to facilitate the tracking of the catheter 506 positional within the heart, geometry sensors 516 may be positioned around the patient's body and configured to sense the position of the catheter 506 within the heart. For example, in some embodiments, the catheter 506 may be comprise with a magnetic element that can be sensed by the geometry sensors 516 to the to derive catheter positional data that is transmitted to a geometry system 520. The geometry system 520 may be configured to generate geometry data in the form of point cloud data which is then input into the mapping systems 512.

In one embodiment, the sensor array 514 may be configured to provide the sensed electrical information to a corresponding measurement system 522. The measurement system 522 may include control circuitry 524 and signal processing circuitry (not shown) for generating electrical measurement data 526 that describes electrical activity detected by sensors in the sensor array 514. The electrical measurement data 526 may comprise analog and/or digital information. In some embodiments, the control circuitry 524 may be configured to control a data acquisition process for measuring electrical activity of the heart and generating the electrical measurement data 526. The electrical measurement data 526 may be acquired concurrently with the therapy delivered by the therapy system 508.

The mapping system 512 may be configured to combine the electrical measurement data 526 with geometry data generated by the geometry system 520 by applying appropriate processing computations. For example, the mapping system 512 may include a single processing module 528 configured to process the signals generated by the geometry system 520 and measurements system 522. For example, the signal processing module 528 may include an EGM processing module 530 configured to process EGM signals associated with the heart. A visualize relation engine 532 of the mapping systems and 512 may be provisioned with a mapped generator function 534 configured to render various metrics associated with the heart in visual form. For this purpose, the visualization engine 532 outputs mapping data 536 that can be rendered on a display 538 as a graphical map 540 showing various metrics associated with the heart.

By way of example, the geometry data output but the geometry system 520 may comprise a graphical representation of the patient's torso in the form of image data acquired for the patient. In one embodiment, the geometry system 520 may process the image data to extract and segment anatomical features of the heart. Additionally, positional information for the sensors within the electrical sensor array 514 may be included in the geometry data. The geometry data may be converted into a two-dimensional or three-dimensional graphical representation that includes regions of interest within the patient's heart by the mapping systems 512.

In other embodiments, the geometry data may include a mathematical model of the patient's heart instructed based on image data for the patient. Anatomical or other landmarks, including locations for the electrodes within the sensor array 514 may be identified in the geometry data to facilitate registration of the electrical measurement data 526. Identification of said landmarks may be performed manually based on the user input, or automatically by means of image processing techniques.

The mapped generator 534 may be configured to generate activation maps for the patient's heart, showing various metrics such as electrical activation times, and indications for QRS onset, the DV/DT, fractionation, etc.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware, such as shown and described with respect to the computer system of FIG. 6.

Figure 6:
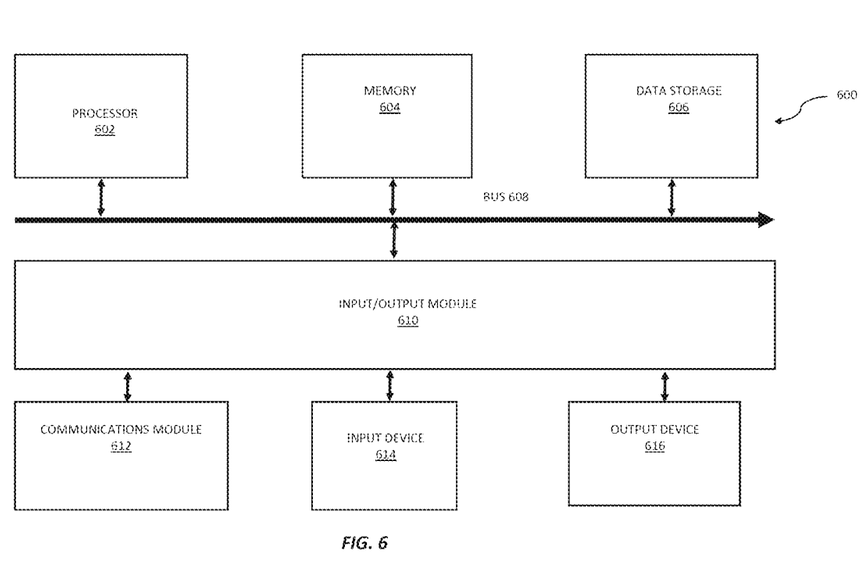
FIG. 6 shows a high-level block diagram of hardware that may be used to practice aspects of the present invention.

FIG. 6 is a block diagram illustrating exemplary hardware for executing some of the techniques disclosed herein, in accordance with one embodiment of the invention. In certain aspects, the computer system 600 may be implemented using hardware or a combination of software and hardware, either in a dedicated server or integrated into another entity or distributed across multiple entities.

Computer system 600 (e.g., client or server) includes a bus 608 or other communication mechanism for communicating information, and a processor 602 coupled with bus 608 for processing information. According to one aspect, the computer system 600 may be implemented as one or more special-purpose computing devices. The special-purpose computing device may be hard-wired to perform the disclosed techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques. By way of example, the computer system 600 may be implemented with one or more processors 602. Processor 602 may be a general-purpose microprocessor, a microcontroller, a Digital Signal Processor (DSP), an ASIC, a FPGA, a Programmable Logic Device (PLD), a controller, a state machine, gated logic, discrete hardware components, or any other suitable entity that can perform calculations or other manipulations of information.

Computer system 600 can include, in addition to hardware, code that creates an execution environment for the computer program in question, e.g., code that constitutes processor firmware, a protocol stack, a database management system, an operating system, or a combination of one or more of them stored in an included memory 604 such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 608 for storing information and instructions to be executed by processor 602. The processor 602 and the memory 604 can be supplemented by, or incorporated in, special purpose logic circuitry. Expansion memory may also be provided and connected to computer system 600 through input/output module 610, which may include, for example, a SIMM (Single in Line Memory Module) card interface. Such expansion memory may provide extra storage space for computer system 600 or may also store applications or other information for computer system 600. Specifically, expansion memory may include instructions to carry out or supplement the processes described above and may include secure information also. Thus, for example, expansion memory may be provided as a security module for computer system 600 and may be programmed with instructions that permit secure use of computer system 600. In addition, secure applications may be provided via the SIMM cards, along with additional information. such as placing identifying information on the SIMM card in a non-hackable manner.

The instructions may be stored in the memory 604 and implemented in one or more computer program products, i.e., one or more modules of computer program instructions encoded on a computer readable medium for execution by, or to control the operation of, the computer system 600, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages; interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, embeddable languages, and xml-based languages. Memory 604 may also be used for storing temporary variable or other intermediate information during execution of instructions to be executed by processor 602.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 670 further includes a data storage device 606 such as a magnetic disk or optical disk, coupled to bus 608 for storing information and instructions. Computer system 600 may be coupled via input/output module 610 to various devices. The input/output module 610 can be any input/output module. Example input/output modules 610 include data ports such as USB ports. In addition, input/output module 610 may be provided in communication with processor 602, so as to enable near area communication of computer system 600 with other devices. The input/output module 610 may provide, for example, for wired communication in some implementations, or for wireless communication in other implementations, and multiple interfaces may also be used. The input/output module 610 is configured to connect to a communications module 612. Example communications modules 612 include networking interface cards, such as Ethernet cards and modems.

The components of the system can be interconnected by any form or medium of digital data communication, e.g., a communication network. The communication network can include, for example, any one or more of a PAN, a LAN, a CAN, a MAN, a WAN, a BBN, the Internet, and the like. Further, the communication network can include, but is not limited to, for example, any one or more of the following network topologies, including a bus network, a star network, a ring network, a mesh network, a star-bus network, tree or hierarchical network, or the like.

For example, in certain aspects, communications module 612 can provide a two-way data communication coupling to a network link that is connected to a local network. Wireless links and wireless communication may also be implemented. Wireless communication may be provided under various modes or protocols, such as GSM (Global System for Mobile Communications), Short Message Service (SMS), Enhanced Messaging Service (EMS), or Multimedia. Messaging Service (MMS) messaging, CDMA (Code Division Multiple Access), Time division multiple access (TDMA), Personal Digital Cellular (PDC), Wideband CDMA, General Packet Radio Service (CPRS), or LTE (Long-Term Evolution), among others. Such communication may occur, for example, through a radio-frequency transceiver. In addition, short-range communication may occur, such as using a Bluetooth, Wi-Fi, or other such transceiver.

In any such implementation, communications module 612 sends and receives electrical, electromagnetic or optical signals that carry digital data streams representing various types of information. The network link typically provides data communication through one or more networks to other data devices. For example, the network link of the communications module 612 may provide a connection through local network to a host computer or to data equipment operated by an Internet Service Provider (ISP). The ISP in turn provides data communication services through the world-wide packet data communication network now commonly referred to as the Internet. The local network and Internet both use electrical, electromagnetic or optical signals that carry digital data streams. The signals through the various networks and the signals on the network link and through communications module 612, which carry the digital data to and from computer system 600, are example forms of transmission media.

Computer system 600 can send messages and receive data, including program code, through the network(s), the network link and communications module 612. In the Internet example, a server might transmit a requested code for an application program through Internet, the ISP, the local network and communications module 610. The received code may be executed by processor 602 as it is received, and/or stored in data storage 606 for later execution.

In certain aspects, the input/output module 610 is configured to connect to a plurality of devices, such as an input device 612 (e.g., input device 614) and/or an output device 614 (e.g., output device 614). Example input devices 612 include a stylus, a finger, a keyboard and a pointing device, e.g., a mouse or a trackball, by which a user can provide input to the computer system 600. Other kinds of input devices 612 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 614 include display devices, such as a LED (light emitting diode), CRT (cathode ray tube), LCD (liquid crystal display) screen, a TFT LCD (Thin-Film-Transistor Liquid Crystal Display) or an OLED (Organic Light Emitting Diode) display, for displaying information to the user. The output device 614 may comprise appropriate circuitry for driving the output device 614 to present graphical and other information to a user.

According to one aspect of the present disclosure, the techniques disclosed here in may be implemented on the computer system 600 in response to processor 602 executing one or more sequences of one or more instructions contained in memory 604. Such instructions may be read into memory 604 from another machine-readable medium, such as data storage device 606. Execution of the sequences of instructions contained in main memory 604 causes processor 602 to perform the process steps described herein. One or more processors in a multi-processing arrangement may also be employed to execute the sequences of instructions contained in memory 604. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components.

Computing system 600 can include clients and servers. A client and server are generally remote from each other and typically interact through a communication network. The relationship of client and server arises by virtue of computer programs running on the respective computers and having a client-server relationship to each other. Computer system 600 can be, for example, and without limitation, a desktop computer, laptop computer, or tablet computer. Computer system 600 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer-readable medium" as used herein refers to any medium or media that participates in providing instructions or data to processor 602 for execution. The term "storage medium" as used herein refers to any non-transitory media that store data and/or instructions that cause a machine to operate in a specific fashion. Such a medium may take many forms, including, but not limited to, non-volatile media, volatile media, and transmission media. Non-volatile media include, for example, optical disks, magnetic disks, or flash memory, such as data storage device 606. Volatile media include dynamic memory, such as memory 604. Transmission media include coaxial cables, copper wire, and fiber optics, including the wires that comprise bus 608. Common forms of machine-readable media include, for example, floppy disk, a flexible disk, hard disk, magnetic tape, any other magnetic medium, a CD-ROM, DVD. any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter affecting a machine-readable propagated signal, or a combination of one or more of them.

As used in this specification of this application, the terms "computer-readable storage medium" and "computer-readable media" are entirely restricted to tangible, physical objects that store information in a form that is readable by a computer. These terms exclude any wireless signals, wired download signals, and any other ephemeral signals. Storage media is distinct from but may be used in conjunction with transmission media. Transmission media participates in transferring information between storage media. For example, transmission media includes coaxial cables, copper wire and fiber optics, including the wires that comprise bus 608. Transmission media can also take the form of acoustic or light waves, such as those generated during radio-wave and infra-red data communications. Furthermore, as used in this specification of this application. the terms "computer", "server", "processor", and "memory" all refer to electronic or other technological devices. These terms exclude people or groups of people. For the purposes of the specification, the terms display or displaying means displaying on an electronic device.

To illustrate the interchangeability of hardware and software, items such as the various illustrative blocks, modules, components, methods, operations, instructions, and algorithms have been described generally in terms of their functionality. Whether such functionality is implemented as hardware, software or a combination of hardware and software depends upon the particular application and design constraints imposed on the overall system. Skilled artisans may implement the described functionality in varying ways for each particular application.

As used herein, the phrase "at least one of" preceding a series of items, with the terms "and" or "or" to separate any of the items, modifies the list as a whole, rather than each member of the list (i.e. each item). The phrase "at least one of" does not require selection of at least one item; rather. the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

To the extent that the term "include," "have," or the like is used in the description or the claims, such term is intended to be inclusive in a manner similar to the term "comprise" as "comprise" is interpreted when employed as a transitional word in a claim. Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description. No claim element is to be construed under the provisions of 35 U.S.C. § 112, sixth paragraph, unless the element is expressly recited using the phrase "means for" or, in the case of a method claim, the element is recited using the phrase "step for."

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

The subject matter of this specification has been described in terms of particular aspects, but other aspects can be implemented and are within the scope of the following claims, For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. In certain circumstances, multitasking and parallel processing may he advantageous. Moreover, the separation of various system components in the aspects described above should not be understood as requiring such separation in all aspects, and it should be understood that the described program components and systems can generally be integrated together in a single software product or packaged into multiple software products.

The title, background, brief description of the drawings, abstract, and drawings are hereby incorporated into the disclosure and are provided as illustrative examples of the disclosure, not as restrictive descriptions. it is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description. with each claim standing on its own as a separately claimed subject matter.

The claims are not intended to he limited to the aspects described herein but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

We claim:

1. A method for generating point cloud data for electro-anatomical mapping, the method comprising:
   receiving from a catheter positioned within a heart point cloud data comprising a plurality of data points (X, Y, and Z) generated pursuant to a data collection step;
   generating surface mesh data to represent a geometry of a myocardial surface, wherein the surface mesh data comprises one or more mesh points arranged to define triangles on the myocardial surface;
   mapping the point cloud data to the surface mesh data, wherein each data point in the point cloud data is mapped to a corresponding data point in the surface mesh data as follows:
   (a) for each data point (X,Y,Z) of the surface mesh data that cannot be mapped to a point cloud data because there is a missing data point (X,Y,Z) in the point cloud data:
   performing an interpolation operation based on the point cloud data within the neighbourhood of the missing data point (X,Y,Z) to generate a value for the missing data point (X,Y,Z); and
   (b) repeating step (a) multiple times N, wherein each time the interpolation for the missing data point is repeated, a check is performed to compare a difference between the value for the missing data point (X,Y,Z) generated from the current iteration and the value for the missing data point (X,Y,Z) generated from the immediately preceding iteration; until the difference is below a threshold.

2. The method of claim 1, wherein N is at least 10,000.

3. The method of claim 1, wherein the point cloud data is generated by a catheter comprising a magnetic field-sensing tip in contact with the myocardial surface.

4. The method of claim 3, wherein the point cloud data comprises a unipolar signal generated by the catheter.

5. The method of claim 3, wherein the point cloud data comprises a bipolar signal generated by the catheter.

6. The method of claim, 1 wherein the point cloud data represents metrics selected from the group comprising activation times, and voltages.

7. A system for generating point cloud data for electro-anatomical mapping, the system comprising:
   electrical system for recording signal data from a probe when the probe is positioned in a heart of a living subject;
   a memory;
   a processor coupled to the memory, wherein the processor is configured to execute instructions stored in the memory to:
   receive point cloud data from the probe, said data comprising a plurality of data points (X, Y, and Z) generated pursuant to a data collection step;
   generate surface mesh data to represent a geometry of a myocardial surface, wherein the surface mesh data comprises one or more mesh points arranged to define triangles on the myocardial surface;
   map the point cloud data to the surface mesh data, wherein each data point in the point cloud data is mapped to a corresponding data point in the surface mesh data as follows:
   (a) for each data point (X,Y,Z) of the surface mesh data that cannot be mapped to a point cloud data because there is a missing data point (X,Y,Z) in the point cloud data:
   perform an interpolation operation based on the point cloud data within the neighbourhood of the missing data point (X,Y,Z) to generate a value for the missing data point (X,Y,Z); and
   (b) repeat step (a) multiple times N, wherein each time the interpolation for the missing data point (X,Y,Z) is repeated, a check is performed to compare a difference between the value for the missing data point (X,Y,Z) generated from the current iteration and the value for the missing data point (X,Y,Z) generated from the immediately preceding iteration; until the difference is below a threshold.

8. The system of claim 7, wherein N is at least 10,000.

9. The system of claim 7, wherein the point cloud data is generated by a catheter comprising a magnetic field-sensing tip in contact with the myocardial surface.

10. The system of claim 9, wherein the point cloud data comprises a unipolar signal generated by the catheter.

11. The system of claim 9, wherein the point cloud data comprises a bipolar signal generated by the catheter.

12. The system of claim, 7 wherein the point cloud data represents metrics selected from the group comprising activation times, and voltages.

* * * * *